(12) United States Patent
Steward et al.

(10) Patent No.: US 8,741,874 B2
(45) Date of Patent: Jun. 3, 2014

(54) INSECTICIDAL COMPOSITIONS WITH DISINFECTANT

(75) Inventors: V. Bruce Steward, Overland Park, KS (US); Steve Fasano, Chapel Hill, NC (US); Guillaume Raymond Huchet, Lawrence, KS (US)

(73) Assignee: Bayer CropScience LP, Research Triangle Park, NC (US)

( * ) Notice: Subject to any disclaimer, the term of this patent is extended or adjusted under 35 U.S.C. 154(b) by 997 days.

(21) Appl. No.: 11/936,325

(22) Filed: Nov. 7, 2007

(65) Prior Publication Data

US 2009/0118367 A1    May 7, 2009

(51) Int. Cl.
*A01P 15/00* (2006.01)
*A01N 53/10* (2006.01)

(52) U.S. Cl.
USPC .......................................... 514/65; 514/531

(58) Field of Classification Search
USPC ........................................................ 424/65
See application file for complete search history.

(56) References Cited

U.S. PATENT DOCUMENTS

| | | | | |
|---|---|---|---|---|
| 1,816,441 A | * | 7/1931 | Peet | 514/547 |
| 4,795,640 A | * | 1/1989 | Helfenberger | 424/405 |
| 4,994,473 A | * | 2/1991 | Broadhurst | 514/335 |
| 5,004,493 A | | 4/1991 | Norris | |
| 5,218,002 A | | 6/1993 | Stroech et al. | |
| 5,773,016 A | * | 6/1998 | Nelson | 424/405 |
| 5,792,465 A | * | 8/1998 | Hagarty | 424/405 |
| 5,827,522 A | * | 10/1998 | Nowak | 424/405 |
| 6,270,784 B1 | | 8/2001 | Mrusek et al. | |
| 2003/0235601 A1 | * | 12/2003 | Hallahan | 424/405 |
| 2006/0166898 A1 | * | 7/2006 | Chen | 514/22 |

FOREIGN PATENT DOCUMENTS

| | | |
|---|---|---|
| EP | 0 524 411 | 6/1992 |
| GB | 2 354 771 | 4/2001 |
| JP | 2005272443 | 10/2005 |

* cited by examiner

*Primary Examiner* — Janet Epps-Smith
*Assistant Examiner* — Audrea Buckley

(57) ABSTRACT

Insecticidal compositions having insecticide and disinfectant activity are provided. Preferably, the insecticidal composition contains both an insect control agent and a disinfectant. Particularly low levels (i.e., below 20%) of at least one hydrocarbon are introduced as a solvent. The insecticidal compositions further comprise an emulsifier, buffer and antifoaming agent. These insecticidal compositions are particularly suitable for delivery in a spray for non-industrial environments. In use, the present insecticidal compositions may be applied directly to or in or around any area where it is desired to control pestiferous insects and the fungi, bacteria, viruses and other contaminants associated with them.

20 Claims, No Drawings

INSECTICIDAL COMPOSITIONS WITH DISINFECTANT

BACKGROUND OF THE INVENTION

1. Field of the Invention

The present invention relates generally to insecticides. More specifically, the present invention relates to insecticidal compositions comprising a disinfectant and/or disinfectant functionality.

2. Description of Related Art

Various insecticides are currently available on the market for both industrial and home use. Historically, insecticides have been used to control insect populations by killing the insect without regard for the fact that insects can serve as vectors for disease even after death. Additionally, there has been a recent resurgence of insect-borne diseases such as malaria, dengue fever, yellow fever, as well as a migration of diseases such as west nile virus into areas of the globe where such diseases were thought to be eradicated. This resurgence has been attributed, in part, to increased insect resistance to insecticides and changes in the climate. Therefore, there exists a need for insecticide compositions that not only result in insect mortality upon use, but prevent or reduce the presence of fungi, bacteria, viruses and other contaminants which cause disease and are associated with insects and the environments where insects reside. The present invention provides such compositions, as well as methods of using the same.

SUMMARY OF THE INVENTION

Insecticidal compositions having disinfectant activity are provided. The insecticidal compositions advantageously comprise at least one insect control agent, disinfectant, emulsifier, buffer and antifoaming agent. Preferably, the insect control agent is at least one pyrethroid, pyrethrin, or a combination thereof. The disinfectant is preferably at least one phenolic compound such as phenylphenol, o-phenylphenol, o-phenyl phenate, or 2-phenylphenate. The disinfectant prevents the formation of fungi, bacteria, viruses and other contaminants associated with pestiferous insects. An anti-foaming agent such as a silicone or polydimethylsiloxane emulsion can be utilized to enhance spraying performance. Various emulsifiers and buffers may be added to stabilize the insecticidal composition. Low levels of a hydrocarbon solvent such as oxo-heptyl acetate or oxo-decyl are also typically employed. Preferably, the insecticidal composition is at least 80% water but this amount can vary as desired.

Methods of killing insects are also provided. The present insecticidal compositions may be applied in any desired manner, such as directly to or in the habitat of a variety of insects found in or around a dwelling.

The foregoing and other aspects of the present invention are explained in detail in the detailed description and examples set forth below.

DETAILED DESCRIPTION OF THE INVENTION

In one embodiment, the present invention provides an insecticidal composition having disinfectant activity. In a preferred embodiment, the insecticidal composition contains both an insect control agent and a disinfectant. Particularly low levels (i.e., below 20%) of a hydrocarbon are typically introduced as a solvent. In a more preferred embodiment, the insecticidal compositions further comprise at least one emulsifier, buffer, antifoaming agent and aqueous diluent.

An insecticidal composition of the present invention is particularly suitable for delivery in a spray formulation due to the unique chemistry and composition of the components contained therein. This is important, inter alia, because the use of aerosols can present numerous problems in terms of application and safety. Thus, being able to formulate product having both insecticidal and disinfectant properties is highly beneficial and is something that was not expected to have been capable of being done given the current state of the art. Preferably, the present insecticidal compositions are applied directly to or in the habitat of any insect found in or around any area such as dwellings, commercial areas, public parks, and the like to control the pestiferous insects and the fungi, bacteria, viruses and other contaminants associated with the pestiferous insects.

The insecticidal compositions according to the present invention include at least one insect control agent. The insect control agent is any compound or composition having insecticidal activity. In a preferred embodiment, the insect control agent comprises pyrethroid, pyrethrin, or a combination thereof. More preferably, the insect control agent comprises at least one pyrethroid such as allethrin, d-allethrin, d-trans allethrin, alfoxylate, bioresmethrin, cyfluthrin, beta-cyfluthrin, cyhalothrin, lambda cyhalothrin, gamma cyhalothrin, bifenthrin, cypermethrin, beta cypermethrin, zeta cypermethrin, cyphenothrin, deltamethrin, tetramethrin, esfenvalerate, fenfluthrin, fenopropathrin, fenpyrithrin, fenvalerate, fluorocythrin, furamethrin, fluvalinate, imiprothrin, permethrin, phencyclate, phenothrin, prallethrin, resmethrin, s-bioallethrin, tau-fluvalinate, tefluthrin, tetrallethrin, tralocythrin and tralomethrin or a combination thereof. Most preferably, the insect control agent is a beta-cyfluthrin (CAS No. 68359-37-5) such as those compositions marketed as TEMPO ULTRA (registered trademark of Bayer AG of Germany) available from Bayer Environmental Science of Research Triangle Park, N.C. Combinations of the above-listed chemicals and agents, as well as other chemicals and agents known to be effective against insects are within the scope and spirit of the present invention.

In another embodiment, the insect control agent further comprises at least one insect development inhibitor such as lufenuron, RH 5849 (2-benzoyl-1-(1,1-dimethylethylbenzoic hydrazide), chlorfluazuron, diflubenzuron, N-[[[3,5-dichloro-4-(4-chlorophenoxy)phenyl]amino]carbonyl]-2,6-difluorobenzamide; flufenoxuron; flucycloxuron; penfluron; teflubenzuron; hexaflumuron; tebufenozide; 2-chloro-N-[[[4-(1-phenylethoxy)-phenyl]-amino]-carbonyl]-benzamide; sodium 1,4-bis-(2-ethylhexyl)-sulphobutanedioate; novaluron, 2-chloro-N-[[[4-(2,2-dichloro-1,1-difluoroethoxy)-phenyl]-amino]-carbonyl]-benzamide; 6-azido-N-cyclopropyl-N'-ethyl-1,3,5-triazine-2,4-diamine; N-[[[5-(4-bromophenyl)-6-methyl-2-pyrazinyl]-amino]-carbonyl]-2, 6-dichloro benzamide; 2,6-dichloro-N-[[(4-chlorophenyl) amino]-carbonyl]-benzamide; methoprene; triflumuron; pyriproxifen; or fenoxycarb or combinations thereof. In such an embodiment, particularly preferred active compound combinations consist of transfluthrin, allethrin or pyrethrum along with fenoxycarb, pyriproxyfen, triflumuron, flufenoxuron and/or methoprene. Very particularly preferred active compound combinations are those containing transfluthrin and triflumuron and, optionally, flufenoxuron. The combination of these active compounds can combine to provide knock-down action and flushing effect with a residual action of over several weeks without a gap in the effect.

The insecticidal compositions of the present invention preferably contain at least one insect control agent in the amount of about 0.01 to 10% by weight of the entire formulation. More preferably, the insect control agent is present in the amount of about 0.02 to 1.0% by weight. Most preferably, the insect control agent is present in the amount of about 0.05% by weight.

Preferably, the insecticidal compositions further include a disinfectant. A disinfectant as contemplated by the present invention is a compound or composition that includes at least one compound or composition effective in treating undesirable contaminants such as fungi, bacteria, viruses and other contaminants associated with pestiferous insects and the environment where pestiferous insects reside. Such an environment includes household surfaces such as tile, glass, wood, laminates, plastics, stone, concrete and similar surfaces, as well as soil and mulch. In a preferred embodiment, the disinfectant includes at least one of benzylalkonium chloride or its other salts, disodium octaborate tetrahydrate-containing compositions, Copper 8 quinolinolate, chromated copper arsenate (CCA), ammoniacal copper quaternary (ACQ) compounds comprising quaternary ammonium chloride containing compositions, copper azole (CA), isothiazolin, disodium octoborate tetrahydrate, borate-containing compositions, acticide 45, hypochlorous acid, sodium percarbonate, zinc oxide, titanium dioxide, sodium salts (CAS No. 7681-52-9), sodium hydroxide (CAS No. 1310-73-2), or combinations thereof. More preferably, the disinfectant includes phenylphenol, o-phenylphenol, o-phenyl phenate, 2-phenylphenate, alone or in combination as well as sodium salts thereof. Most preferably, the disinfectant includes o-phenylphenol (CAS No. 132-27-4) compositions such as those marketed as PREVENTOL ON EXTRA available from Lanxess Corporation of Pittsburgh, Pa .(PREVENTOL is a registered trademark of Lanxess Deutschland of Leverkusen, Germany). Combinations of the above-listed chemicals and agents, as well as other chemicals and agents known to be effective against fungi, bacteria, viruses and other contaminants are within the scope and spirit of the present invention.

The insecticidal compositions of the present invention preferably contain at least one disinfectant in the amount of about 0.1 to 1% by weight of the entire formulation. More preferably, the disinfectant is present in the amount of about 0.2 to 0.5% by weight. Most preferably, the disinfectant is present in the amount of about 0.3% by weight.

In one embodiment, the insecticidal compositions of the present invention include at least one of a variety of hydrocarbon solvents. Suitable solvents include aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. Especially preferred is oxo-heptyl acetate marketed as EXXATE 700 or oxo-decyl acetate marketed as EXXATE 1000, alone or in combination, which are each supplied by ChemCentral Corporation of Bedford Park, Ill. (both registered trademarks of Exxon Mobil Corporation) or combinations thereof.

Preferably, the hydrocarbon solvent is employed at low levels to reduce both flammability and environmental impact while improving user safety. The solvent is preferably maintained at levels below 20% by weight of the entire insecticidal composition. In one embodiment of the present insecticidal composition, the solvent is present in the amount of about 0.1 to 0.5% by weight. More preferably, the solvent is present in the amount of about 0.2 to 0.4% by weight. Most preferably, the solvent is present in the amount of about 0.3% by weight.

In one embodiment of the present invention, the insecticidal composition includes at least one emulsifier. The emulsifier is added to the composition to stabilize the entire composition by improving water solubility and preventing phase separation from the time of production until use. The emulsifier may be a cationic, anionic, amphoteric or nonionic detergent as well as a combination thereof.

Suitable nonionic detergents include isopropylamine sulfonate, tristyrlyphenol, tristyrylphenol ethoxylate, polyethoxylates derived from primary and secondary aliphatic alcohols having from 8 to 24 carbons atoms in the alcohol alkyl chain or any combination thereof. Still other suitable nonionic detergents are polyoxyalkylene alkyl phenols, polyalkylene esters, polyalkylene alkyl amines, polyalkylene alkyl amides, fatty acid esters of glycols, polyalkylene oxide block copolymers or combinations thereof. Suitable anionic detergents include alkyl aryl sulfonates, fatty acid soaps, fatty sulfates, alkyl sulfonates, alkali metal salts, alkali metal dialkyl sulfosuccinates, ethoxylated alcohol sulfates, phosphate esters, taurates or a combination thereof.

In a preferred embodiment, the emulsifier is a mixture of an anionic and a nonionic detergent. When an anionic emulsifier is used in addition to an nonionic emulsifier, the amount of emulsifier required may be lowered, especially in the present insecticidal compositions comprising at least one pyrethroid. This combination of emulsifiers further allows compositions comprising higher active compound concentrations to be prepared.

Preferably, the emulsifier is a mixture of anionic/nonionic detergent blends such as those marketed as TOXIMUL S-A and TOXIMUL R-A (registered trademarks of Stepan Chemical of Northfield, Ill.) which are each present in the amount of less than 2% by weight. More preferably, each emulsifier is present in the amount of about 0.09 to 0.15% by weight. Most preferably, each emulsifier is present in the amount of about 0.11 to 0.13% by weight.

In one embodiment, the insecticidal composition also includes at least one buffer. Preferably, the buffer is used to adjust the pH to a neutral range of about 6 to 8. Any suitable buffer may used to maintain the pH within this range. Preferably, the buffer is at least one acid such as citric or phosphoric acid. A neutral pH helps reduce the incidence of corrosion, burn or otherwise harmful affects to innate surfaces which may come into contact the insecticidal composition of the present invention. Additionally, the buffer ensures chemical stability of the insecticide.

Preferably, the insecticidal composition includes at least one buffer present in the amount of about 0.01 to 0.2% by weight. More preferably, the insecticidal composition includes at least one buffer present in the amount of about 0.05 to 0.15% by weight. Most preferably, at least one buffer is present in the amount of about 0.07% by weight.

Preferably, the insecticidal compositions also includes at least one anti-foaming agent to reduce bubble formation and improve spraying performance. An anti-foaming agent is any compound or composition capable of inhibiting or reducing the formation of bubbles. The anti-foaming agent inhibits bubble formation by reducing the surface tension of the liquid composition. Preferably, the present insecticidal compositions contain at least one anti-foaming agent such as silicone, organic phosphate, alcohol, glycol or a combination thereof. Most preferably, the anti-foaming agent is at least one silicone composition, alone or in combination, such as those marketed as SAG 30 (registered trademark of GE Silicones)

or Antifoam 8830 FG/IND that are available from Harcros Chemicals, Incorporated of Kansas City, Kans.

In an alternative embodiment, a mixture of alcohols is employed as the anti-foaming agent. Suitable alcohols include 1-octanol, 1-hexanol, 1-pentanol, 1-butanol, or combinations thereof. Optionally, one or more glycols such as hexylene glycol, triethylene glycol, or 1,4-butanediol may be added.

In one embodiment of the present insecticidal composition, the anti-foaming agent is present in the amount of about 0.01 to 0.15% by weight. More preferably, the anti-foaming agent is present in the amount of about 0.02 to 0.08% by weight. Most preferably, the anti-foaming agent is present in the amount of about 0.03% by weight.

According to the present invention, the insecticidal compositions are largely comprised of water. Deionized water is preferred for the above compositions, however, normal tap water may be used. In one embodiment, water comprises at least 80% of the entire insecticidal composition, Preferably, water is present in the amount of about 90.0% to 99.9% by weight. Most preferably, water is present in the amount of about 98.8%.

Standard additives that inhibit corrosion, synergists and fragrances can also be introduced to the present insecticidal composition. Synergists may increase the overall effectiveness of the insecticides. Suitable synergists include piperonyl butoxide, sesamax, dodecyl imidazole, safroxan, or combinations thereof. Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be added to the present insecticidal compositions. Other suitable additives include mineral and vegetable oils.

Stabilizers and antioxidants can be added and include sulfites or metabisulfites, such as potassium metabisulfite, organic acids, such as citric acid and ascorbic acid, inorganic acids, such as hydrochloric acid or sulfuric acid, and phenols, such as butylhydroxytoluene, butylhydroxyanisole and tocopherol. Preferably, the stabilizers and antioxidants are present in the amount of about 0.1% to 2.0% by weight. Preservatives can also be added and can include formaldehydes or formaldehyde-releasing agents and derivatives of benzoic acid, such as p-hydroxybenzoic acid.

Optionally one or more inorganic pigments can be added for color such as iron oxide, titanium oxide and Prussian Blue, and organic dyestuffs, such as alizarin dyestuffs, azo dyestuffs and metal phthalocyanine dyestuffs. Preferably, the one or more pigments are present in the amount of about 0.001% to 1.0% by weight. Other additives that can be added include trace nutrients such as salts of iron, manganese, boron, copper, cobalt, molybdenum and zinc.

The insecticidal compositions according to the present invention can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances. These formulations are produced in a known manner, for example by mixing the active compounds (i.e., the insect control agent and disinfectant) with extenders, that is liquid solvents and/or solid carriers, optionally with a hydrocarbon solvent which is less than about 20% by weight based on the total weight of the insecticidal composition, optionally with an emulsifier which is less than 2% by weight, optionally with a buffer, optionally with an anti-foaming agent, and water.

In one embodiment, the insecticidal compositions of the present invention may be combined with a gaseous propellant, pressurized and spayed from an aerosol can. In a preferred embodiment, the insecticidal compositions of the present invention are presented in a ready-to-use formulation and enclosed in a pump spray container for non-industrial applications. The insecticidal compositions of the present invention, especially those in a spray formulation, are particularly advantageous for non-industrial use by the lay consumer. The presence of a disinfectant such as those described above allows the consumer to simply spray or otherwise project the present insecticidal compositions onto a surface or into an area or environment where insects are known to reside, or directly on the insect itself. The user may refrain from wiping or cleaning the treatment area after spraying in an effort to reduce or inhibit microbial formation on the treated surface. Furthermore, the user may apply the present insecticidal compositions in areas of their home, such as basements or bathrooms, that may provide an environment that fosters both the development of insects and microbial or pathogenic growth associated with such pestiferous insects. Still further, the insecticidal compositions of the present invention exhibit excellent storage stability and very good dispersability in water. In addition, the present insecticidal compositions can be produced at an economical price with low amounts of hydrocarbon solvents resulting in improved user safety.

The insecticidal compositions according to the present invention are suitable for combating arthropod pests, particularly millipedes, centipedes, isopods and arachnids that are encountered in various environments such as in and around the home or a dwelling, in agriculture, in forestry, in the protection of stored products and of materials, and in the hygiene field. The above-mentioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spec.

From the order of the Thysanura, for example, *Lepisma saccharina.*

From the order of the Orthoptera, for example, *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria.*

From the order of the Dermaptera, for example, *Forficula auricularia.*

From the order of the Isoptera, for example, *Reticulitermes* spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrvsorrhoea, Lymantria* spp., *Bucculatrix thurberiella, Phyllocnistis citrella, Agrotis* spp., *Euxoa* spp., *Feltia* spp., *Earias insulana, Heliothis* spp., *Spodoptera exigua, Mamestra brassicae, Panolis flammea, Spodoptera litura, Spodoptera* spp., *Trichoplusia ni, Carpocapsa pomonella, Pieris* spp., *Chilo* spp., *PyTausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera* postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis and Costelytra zealandica.

From the order of the Hymenoptera, for example, Diprion spp., Hoplocampa spp., Lasius spp., Monomorium pharaonis and Vespa spp.

From the order of the Diptera, for example, Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae and Tipula paludosa.

From the order of the Siphonaptera, for example, Xenopsylla cheopis, Ctentocephalides felis, Ceratophyllus spp.

From the order of the Arachnida, for example, Scorpio maurus, Latrodectus mactans.

From the order of Blatteria, for example Blatella germanica.

From the order of Hemiptera, for example insects from the suborder of Coleorrhyncha, Heteroptera, Auchenorryncha and Stemorhyncha.

Advantages of the present invention will be apparent from the description of the examples that follow The following examples exhibit merely a preferred embodiment of the present invention.

Effectiveness Testing on Insects

Experiments were conducted to compare the effectiveness of various known insecticidal compositions available on the market to one embodiment of the presently disclosed insecticidal composition. The active ingredients of the known insecticidal compositions are summarized in Table I. The insecticidal composition of the present invention as tested is summarized in Table II.

TABLE I

| Insecticide/Trade Name | Active Ingredient(s) |
|---|---|
| Ortho Home Defense RTU | 0.05% bifenthrin |
| Spectricide BugStop Home RTU | 0.03% lambda-cyhalothrin |
| Bayer Advanced Home Pest | 0.05% beta-cyfluthrin |
| Bayer Advanced Power Force Carpenter Ant and Termite RTU | 0.02% deltamethrin |
| 0.3% Preventol ON Extra | 0.3% sodium o-phenylphenolate |

TABLE II

| Ingredient | Trade Name | Function | % w/w |
|---|---|---|---|
| Beta-Cyfluthrin | Tempo Ultra Technical | Insecticide | 0.05 |
| Sodium o-phenylphenolate | Preventol ON Extra | Disinfectant | 0.3 |
| Oxo-heptyl acetate | Exxate 700 | Solvent | 0.32 |
| Anionic/nonionic Detergent Blend | TOXIMUL S-A | Emulsifier | 0.13 |
| Anionic/nonionic Detergent Blend | TOXIMUL R-A | Emulsifier | 0.11 |
| Citric Acid | N/A | Buffer | 0.07 |
| Antifoam 8830 FG | N/A | Antifoam | 0.03 |
| Water | N/A | Diluent | 98.99 |

For this set of experiments, selected insects were placed into an enclosure. The bottom of the enclosure was covered with sand to absorb excess liquid treatment spray. Each insecticidal composition was applied directly to the respective insect by holding the sprayer approximately 12 inches from the target pest and pumping the sprayer two times. The species of insect tested and number of insects per replication is summarized in Table III.

TABLE III

| | Species | | | |
|---|---|---|---|---|
| | Carpenter Ant | German Cockroach | House Fly | House Cricket |
| Number/Replication | 5/5 | 10/5 | 10/5 | 10/5 |

The percentage of mortality was recorded at 0.25, 0.5, 1, 2, 6 and 24 hours post application. The results of the testing are set forth below in Table IV. In summary, the insecticidal composition of the present invention (referred to as "Inventive Composition") demonstrated statistically similar mortality effectiveness to the control, the BUG STOP and beta-cyfluthrin for carpenter ants after 15 minutes. for German cockroaches after 15 minutes, the insecticidal composition of the present invention proved numerically superior to all treatments and statistically superior to all compositions except beta-cyfluthrin. For the house fly after 15 minutes, the insecticidal composition of the present invention demonstrated an identical mortality rate (100%) to all compositions except that of the PREVENTOL ON EXTRA (sodium o-phenylphenolate) alone and the control. In the case of the house cricket after 15 minutes, the insecticidal composition of the present invention demonstrated an identical mortality rate to BUG STOP, beta-cyfluthrin and POWER FORCE and was statistically superior to HOME DEFENSE, PREVENTOL ON EXTRA and the control.

TABLE IV

| | % Mortality - 15 Minutes Post Exposure | | | |
|---|---|---|---|---|
| Treatment | Carpenter Ant | German Cockroach | House fly | House cricket |
| Ortho Home Defense | 40 b | 8 d | 100 a | 85 bc |
| Spectricide BugStop | 100 a | 31 cd | 100 a | 100 a |
| Beta-Cyfluthrin | 100 a | 74 ab | 100 a | 100 a |
| Power Force Ant & Termite | 45 b | 46 bc | 100 a | 98 a |
| Inventive Composition | 100 a | 98 ab | 100 a | 100 a |
| Preventol ON Extra | 0 b | 0 d | 15 b | 0 c |
| Control | 0 b | 0 d | 0 c | 0 c |

Beyond 15 minutes, all compositions produced complete mortality. The PREVENTOL ON EXTRA alone was shown to be slightly efficacious against German cockroach (18% at 6 hrs) and highly efficacious against the house fly (81% at 1 hr). The mortality rate average for all species is summarized in Table V.

TABLE V

| | | | | % Mortality - Avg of All Species | | | |
|---|---|---|---|---|---|---|---|
| Hrs | Control | Ortho Home Defense | Spectracide BugStop | Beta-Cy | PF Ant & Termite | Home + Prevent | Preventol ON Extra |
| 0.25 | 0 | 58 | 83 | 94 | 72 | 99 | 4 |
| 0.5 | 1 | 99 | 100 | 100 | 99 | 100 | 14 |
| 1 | 1 | 100 | 100 | 100 | 100 | 100 | 24 |
| 2 | 1 | 100 | 100 | 100 | 100 | 100 | 26 |
| 6 | 1 | 100 | 100 | 100 | 100 | 100 | 26 |
| 24 | 2 | 100 | 100 | 100 | 100 | 100 | 28 |

When beta-cyfluthrin was used in combination with the sodium o-phenylphenolate disinfectant, PREVENTOL ON EXTRA, the speed of kill was increased in some species. Thus, insecticidal compositions comprising both beta-cyfluthrin and sodium o-phenylphenolate were proven effective for killing insects as well as providing a disinfectant to reduce or inhibit formation of mold, mildew, fungi, bacteria, viruses or combinations thereof.

Test of Sanitizer Effectiveness

Testing of the above composition was conducted according to E.P.A. test protocol as a basis for inanimate non-food contact sanitizer label claims. Specifically, the percent reduction in *K pneumoniae* and *S. aureus* bacteria was measured after five minutes of contact for two fresh preparations and one sixty day old preparation. As summarized in Table VI, each composition was shown to effectively reduce populations of *K. pneumoniae* and *S. aureus*.

TABLE VI

| Formula | Age of Preparation | % Reduction K. pneumoniae | % Reduction S. aureus |
|---|---|---|---|
| Beta-cyfluthrin 0.05% + Preventol ON Extra 0.3% | Fresh | 99.9 | >99.9 |
| Beta-cyfluthrin 0.05% + Preventol ON Extra 0.3% | Fresh | 99.9 | >99.9 |
| Beta-cyfluthrin 0.05% + Preventol ON Extra 0.3% | 60 Day | >99.9 | >99.9 |

Having disclosed the subject matter of the present invention, it should be apparent that many modifications, substitutions and variations of the present invention are possible in light thereof. It is to be understood that the present invention can be practiced other than as specifically described. Such modifications, substitutions and variations are intended to be within the scope of the present application. As used in the following claims, articles such as "a", "the" and so on can connote the singular or the plural of the object following.

The invention claimed is:

1. An insecticidal composition comprising
    beta-cyfluthrin in an amount of 0.02 to 1.0% by weight based on the weight of the composition;
    o-phenylphenol or a sodium salt thereof in an amount of 0.2 to 0.5% by weight based on the weight of the composition;
    a hydrocarbon solvent in an amount of less than 20% by weight based on the weight of the composition;
    optionally an emulsifier in an amount of less than 2% by weight;
    optionally a buffer;
    optionally an anti-foaming agent; and
    water.

2. The composition of claim 1, wherein the solvent is selected from the group consisting of hexane, benzene, toluene, xylene, mineral spirits, mineral oil, d-limonene, heavy aromatic naptha, kerosene, paraffins, acetic acid esters, a $C_6$-$C_8$ alkyl ester, and combinations thereof.

3. The composition of claim 1, wherein the solvent comprises oxo-heptyl acetate or oxo-decyl acetate and is present in an amount of 0.2% to 0.4% by weight based on the weight of the composition.

4. The composition of claim 1, wherein the emulsifier comprises a mixture of anionic/nonionic detergent blends wherein each blend component is present in an amount of 0.09 to 0.15% by weight based on the weight of the composition.

5. The composition of claim 1, wherein the buffer comprises citric acid and is present in an amount of 0.05 to 0.15% by weight based on the weight of the composition.

6. The composition of claim 1, wherein the antifoaming agent comprises a silicone or polydimethylsiloxane emulsion and is present in an amount of 0.02 to 0.08% by weight based on the weight of the composition.

7. The composition of claim 1, wherein the composition is in a spray formulation.

8. The composition of claim 1, wherein the composition has a pH of 6 to 8.

9. The composition of claim 1 wherein said water is present in an amount of at least 80% by weight based on the weight of the composition.

10. The composition of claim 1, wherein the water is present in an amount of 90.0% to 99.9% by weight based on the weight of the composition.

11. A method of controlling unwanted insects comprising the steps of
    providing the insecticidal composition of claim 1; and
    applying the composition to the insects or in a habitat capable of being utilized by said insects, in an effective amount.

12. The method of claim 11, wherein the insects are selected from the group consisting of carpenter ants, German cockroaches, house flies, and house crickets.

13. An insecticidal composition comprising
    beta-cyfluthrin in an amount of 0.02 to 1.0% by weight based on the weight of the composition;
    o-phenylphenol or a sodium salt thereof in an amount of 0.2 to 0.5% by weight based on the weight of the composition;
    a hydrocarbon solvent in an amount of less than 20% by weight based on the weight of the composition;
    an emulsifier comprising a mixture of anionic/nonionic detergent blends wherein each blend component is present in an amount of less than 2% by weight based on the weight of the composition;
    optionally a buffer;
    optionally an anti-foaming agent; and
    water.

14. The composition of claim 1, wherein the beta-cyfluthrin is present in an amount of 0.05% by weight based on the weight of the composition.

15. The composition of claim 1, wherein the o-phenylphenol or a sodium salt thereof is present in an amount of 0.30% by weight based on the weight of the composition.

16. The composition of claim 1, wherein
the beta-cyfluthrin is present in an amount of 0.05% by weight based on the weight of the composition, and
the o-phenylphenol or a sodium salt thereof is present in an amount of 0.30% by weight based on the weight of the composition.

17. The composition of claim 1, wherein
the hydrocarbon solvent is present in an amount of 0.1 to 0.5% by weight based on the weight of the composition;
the emulsifier comprises a mixture of anionic/nonionic detergent blends wherein each blend component is present in an amount of 0.09 to 0.15% by weight of the composition;
the buffer is present in an amount of 0.01 to 0.2% by weight of the composition;
the anti-foaming agent is present in an amount of 0.01 to 0.15%; and
the water is present in an amount of 90.0 to 99.9% by weight of the composition.

18. An insecticidal composition consisting essentially of
beta-cyfluthrin in an amount of 0.02 to 1.0% by weight based on the weight of the composition;
o-phenylphenol or a sodium salt thereof in an amount of 0.2 to 0.5% by weight based on the weight of the composition;
a hydrocarbon solvent in an amount of less than 20% by weight based on the weight of the composition;
optionally an emulsifier;
optionally a buffer;
optionally an anti-foaming agent; and
water.

19. An insecticidal composition of claim 18, wherein
the beta-cyfluthrin is present in an amount of 0.05% by weight based on the weight of the composition, and
the o-phenylphenol or a sodium salt thereof is present in an amount of 0.30% by weight based on the weight of the composition.

20. The composition of claim 18 wherein said emulsifier, buffer, and anti-foaming agent are present.

* * * * *